United States Patent [19]

Roi du Maroc, II.

[11] Patent Number: 4,805,631
[45] Date of Patent: Feb. 21, 1989

[54] DEVICE FOR THE DETECTION, THE STUDY AND THE SUPERVISION OF DISEASES, AND IN PARTICULAR HEART DISEASES, RESULTING IN ELECTRICALLY RECORDABLE MANIFESTATIONS

[76] Inventor: Sa Majeste H. Roi du Maroc, II., Palais Royal, Rabat, Morocco

[21] Appl. No.: 849,800

[22] Filed: Apr. 9, 1986

[30] Foreign Application Priority Data

Apr. 9, 1985 [MA] Morocco .................................. 20630

[51] Int. Cl.⁴ .................................................. A61B 5/04
[52] U.S. Cl. ...................................... 128/710; 272/71; 434/254; 128/903
[58] Field of Search ............... 128/903, 695, 696, 710, 128/687, 707, 781; 272/71; 434/254

[56] References Cited

U.S. PATENT DOCUMENTS

| Re. 32,361 | 2/1987 | Duggan | 128/903 |
| 3,583,392 | 6/1971 | Frieberger | 128/687 |
| 4,051,522 | 9/1977 | Healy et al. | 358/86 |

FOREIGN PATENT DOCUMENTS 2402439 4/1979 France .

OTHER PUBLICATIONS

Journal of the Acoustical Society of America, vol. 70, No. 3, 9/81, pp. 683–686, New York, US; B. C. Sonies et al.: "Ultrasonic Visualization of Tongue Motion During Speech".

Electronique et Micro-Electronique Industrielles, No. 227, 11/1/76, pp. 36–39, Paris, FR; J. P. Waymel: "L'electronique au Service de l'electroencephalographie".

Video Kymography: An Improved Method for Electrokymography by B. Lindeberg, Digest of the Third International Conference on Medical Physics, Chalmer University of Technology, Göteborg, Sweden Jul. 30–Aug. 4 1972.

*Primary Examiner*—William E. Kamm
*Assistant Examiner*—George Manuel
*Attorney, Agent, or Firm*—Burns, Doane, Swecker & Mathis

[57] ABSTRACT

A device for observing and recording the activity of at least one organ of the body of a patient producing electrically recordable manifestations for in particular studying and supervising heart diseases, comprises video means (4) for filming and recording movements of the subject, known means (1, 2, 3) for detecting and transmitting the electrocardiogram of the studied subject, and an assembler (6, 7, 8) for receiving and possibly recording together the data received by said video means (4) and by said detecting and transmitting means (1, 2, 3).

12 Claims, 4 Drawing Sheets

DEVICE FOR THE DETECTION, THE STUDY AND THE SUPERVISION OF DISEASES, AND IN PARTICULAR HEART DISEASES, RESULTING IN ELECTRICALLY RECORDABLE MANIFESTATIONS

The present invention relates to a device for the detection, the study and the supervision of diseases, in particular heart diseases, which result in electrically recordable manifestations.

It is known that many diseases or troubles (for example heart or coronary deseases) are detectable by detectors delivering electrically recordable data (for example the electrocardiogram of the patient).

But it is also known that the detection of these diseases, at their most precocious stage, necessitates very prolonged recordings and very often necessitates the knowledge, at the instant at which the manifestations of said diseases are apparent, of the exact physical activity of the supervised subjects.

An object of the present invention is to put at the disposal of doctors and medical research personnel, a device for detecting under the best conditions and by assembling the various necessary elements, the diseases which may result in an electrically recordable manifestation.

The invention therefore provides a device for observing and recording the activity of at least one organ of the body of a patient resulting in electrically recordable manifestations for the purpose of in particular studying and supervising heart diseases, comprising video means for filming the movements of the patient, means for detecting and transmitting electrical signals translating the activity of the considered organ, means for combining the corresponding video signals with the image of the patient and electrical signals translating the activity of said organ, means for recording said combined signals, and means for simultaneously displaying images relating to the movements of the patient and those of the electrical signals translating the activity of said organ, characterized in that the means for detecting and transmitting the electrical signals translating the activity of said organ comprise, in the known manner, sensors fixed to the body of the patient in such manner as to receive the data relating to the activity of this organ and connected to a transmitter carrier by the patient and fed with power by an autonomous electrical power supply, and a receiver for receiving signals from the transmitter, said receiver being connected to an input of a video curve converter having another input which is connected to the output of said filming means, said video curve converter being adapted to permit the synchronized recording and/or observation of the images relating to the motions of the patient filmed by the filming means and those of the diagram as a function of time of the operation of the considered organ, said receiver being moreover connected to an input of a video frequency meter having another input which is connected to the output of said filming means, said video frequency meter being adapted to permit the synchronized recording and/or observation of the images relating to the evolutions of the patient filmed by the filming means, and the numbered data images relating to the operation of the considered organ.

Although the means which constitute the device according to the invention may be physically interconnected, the invention is shown to be of particular interest when the subject to be studied has a complete independence in his exercises and his displacements, which most often implies that it is advisable to provide means permitting the remote transmission of the received data, in particular as concerns the electrocardiogram which will be transmitted to a receiving apparatus and, possibly, a recorder of the television and magnetoscope type of apparatus.

It is also clear that, although in some cases it appears necessary to receive simultaneously, in addition to the image of the patient and his electrocardiogram, complementary data such as the temperature, the state of the skin, etc., it is possible within the scope of the invention to place on the patient a suitable detector for receiving the desired data and transmitting this data to an assembler used in the invention.

As supervising video means, there is employed a video magnetoscope system, essentially comprising a small camera having a system for storing the filmed images. This camera is mounted on a pivotal leg, the orientation of this camera (onto the patient) is achieved by means of a transmitter fixed on the patient who controls one or more servocontrolled motors which constantly orient the camera onto the patient. This camera will record on a portion of the film (for example one half of this film) the displacements and the gestures of the patient.

The means for detecting pulsations of the heart are known and most often there are employed two or three electrodes fixed to the thorax of the patient and receiving potentials of heart operation emitted throughout the heart beats, these electrodes are connected to a small case carried on the waist of the patient and which records the electrocardiogram and transmits it to the magnetoscope described hereinafter, so that the latter in turn records said electrocardiogram on the same film which simultaneously records the activity of the patient. This case is preferably completely sealed since it is often desirable to use the device of the invention when the patient effects swimming movements. Progress in electronics permits at the present time to envisage the elimination of this case and the direct transmission to the camera for recording the data received by each electrode, which data will form the electrocardiogram of the patient.

The assembler is, according to the invention, formed by the camera itself or its film which receives simultaneously the image and electrocardiogram data; this film is projected and it is then possible to simultaneously appreciate the form and intensity of a movement and the modifications brought about by this movement on the electrocardiogram.

A better understanding of the invention will be had from the following description which is given solely by way of example with reference to the accompanying drawings, in which.

Figure 1:
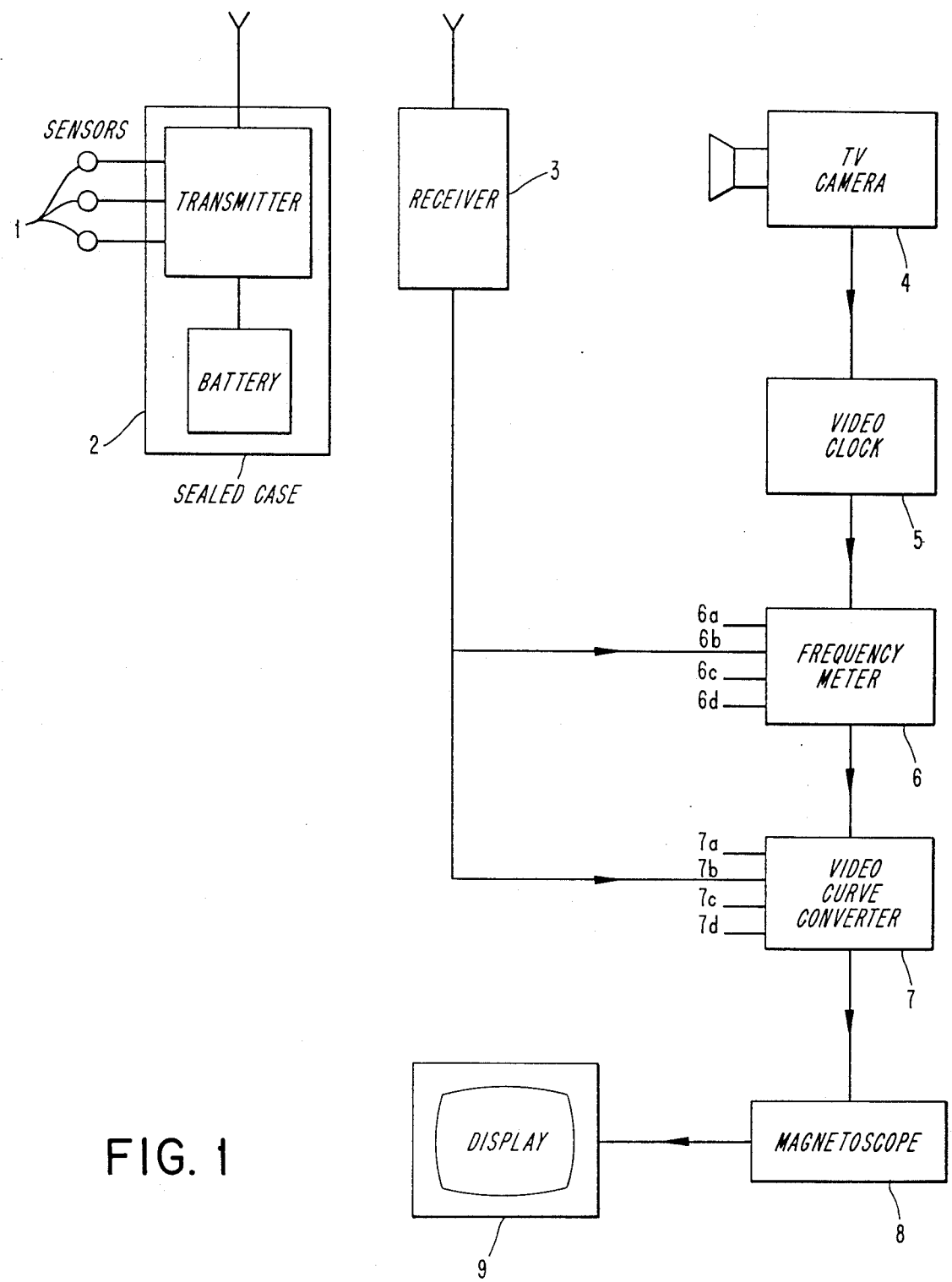
FIG. 1 is a block diagram of a preferred embodiment of the observing and recording device according to the invention.

The observing and recording device shown in FIG. 1 comprises three sensors 1 adapted to be secured to the thorax of a patient for the purpose of detecting the activity of his heart and delivering electrical signals representing this activity.

The sensors 1 are connected to a transmitter 2 fed with power by a battery and carried by the patient, for example on the waist or on the back of the patient.

The transmitter 2 is advantageously placed in a sealed case so that the patient carrying it can swim in a swimming pool.

The device according to the invention further comprises a receiver 3 for the signals transmitted by the transmitter 2 and a television camera 4 adapted to film the motions of the patient whose heart behaviour must be studied.

The camera 4, which is advantageously of the automatically focused, may be carried by an operator whose function is to follow the motions of the patient.

It may also be mounted on a tripod suitably disposed in the zone of motion of the patient and its movements may be controlled in azimuth and in elevation by a device comprising, for example, a small radar tuned to the signals of one of the sensors 1 and controlling corresponding servocontrolled electric motors.

The output of the camera 4 is connected to the input of a video clock 5 adapted to generate synchronization signals for the video signals. The video clock is moreover adapted to deliver indications of date and hour of the examination carried out. It also performs the function of a chronometer for effecting calculations on the portions of the recording which are of particular interest to the practitioner.

The output of the video clock 5 is connected to the input of a video frequency meter 6 whose design will be described in detail with reference to FIG. 2.

The output of the video frequency meter is connected to the input of a video curve converter 7 which will be described in detail with reference to FIG. 4.

The video frequency meter 6 and the video curve converter 7 each comprise an input by which they are connected to the output of the receiver 3 receiving the heart activity signals.

These two devices, or at least one thereof, may comprise additional inputs permitting the association with the video signal relating to the image of the patient, of data relating to the activity of other organs of the patient or to parameters of the equipment in which the patient moves.

These inputs, shown at 6a to 6d and 7a to 7d in FIG. 1, may also receive the heart signals of a plurality of patients or athletes whose reactions under effort are desired to be observed.

The output of the video curve converter 7 is connected to the input of a video track of a magnetoscope 8 whose reading output is connected to a screen display device 9.

It will be understood that it is also possible to connect the display device 9 directly to the output of the video curve converter 7.

In this case, there will be available only data in real time concerning the activity of the patient and the reactions of the studied organ or organs of the latter.

Figure 2:
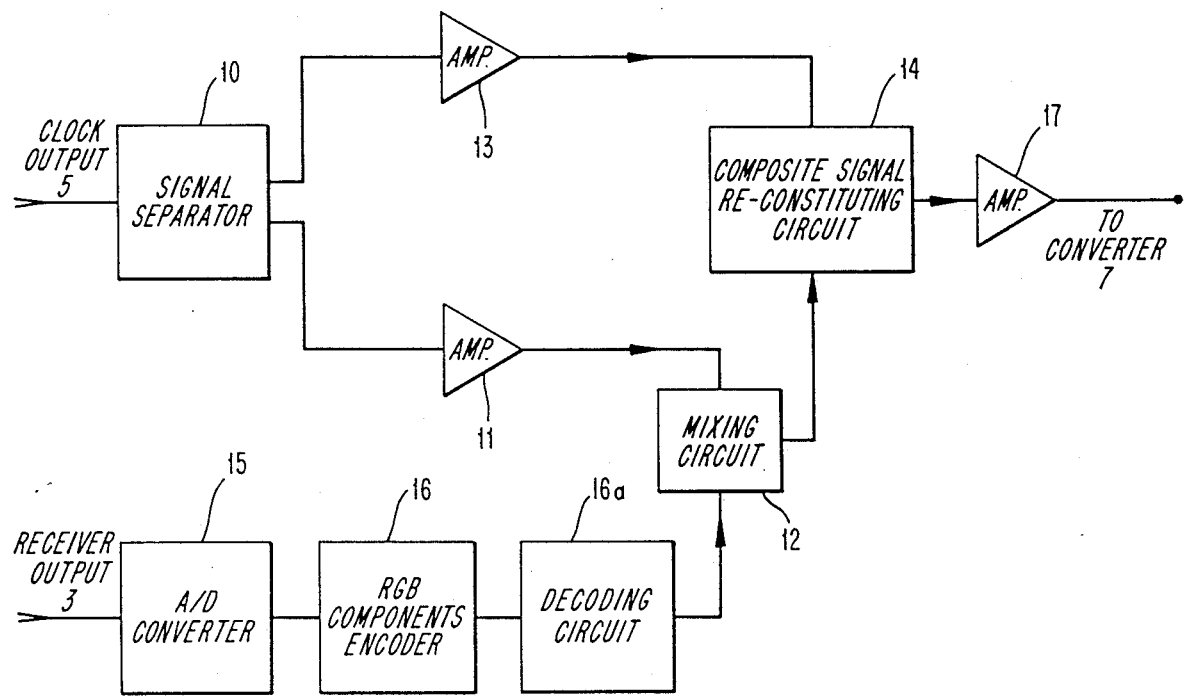
FIG. 2 is a more detailed diagram of the video frequency meter which is part of the construction of the device shown in FIG. 1.

The video frequency meter shown in FIG. 2 is adapted to permit the display simultaneously with that of the image of the motions of the patient of numbered data, such as, for example, the pulse rate, the blood pressure, the temperature or other data.

It mainly comprises a circuit 10 adapted to separate the video signals and synchronization signals making up the output signal of the video clock 5 (FIG. 1).

The video signal output of the circuit is connected through an amplifier 11 to an input of a mixing circuit 12.

The output of the synchronization signal of the circuit 10 is connected through an amplifier 13 to an input of a circuit 14 for re-constituting the composite signal.

The video frequencymeter further comprises an input for the output signal of the receiver 3, signal representing the activity of the organ to be studied.

This input is that of a converter 15 of analog signals into digital signals TTL further comprising a circuit for counting the signals received (not shown).

The output of the converter 15 is connected to the input of a circuit 16 for the video encoding into R, G, B components of the color signal to be obtained.

The output of the circuit 16 is connected to the input of a decoding circuit 16a whose output is connected to another input of the mixing circuit 12.

The output of the mixing circuit is connected to a second input of the circuit 14 reconstituting the composite signal.

The output of the circuit 14 is connected, through an amplifier 17, to the composite signal input of the video curve converter 7 (FIG. 1).

Figure 3:
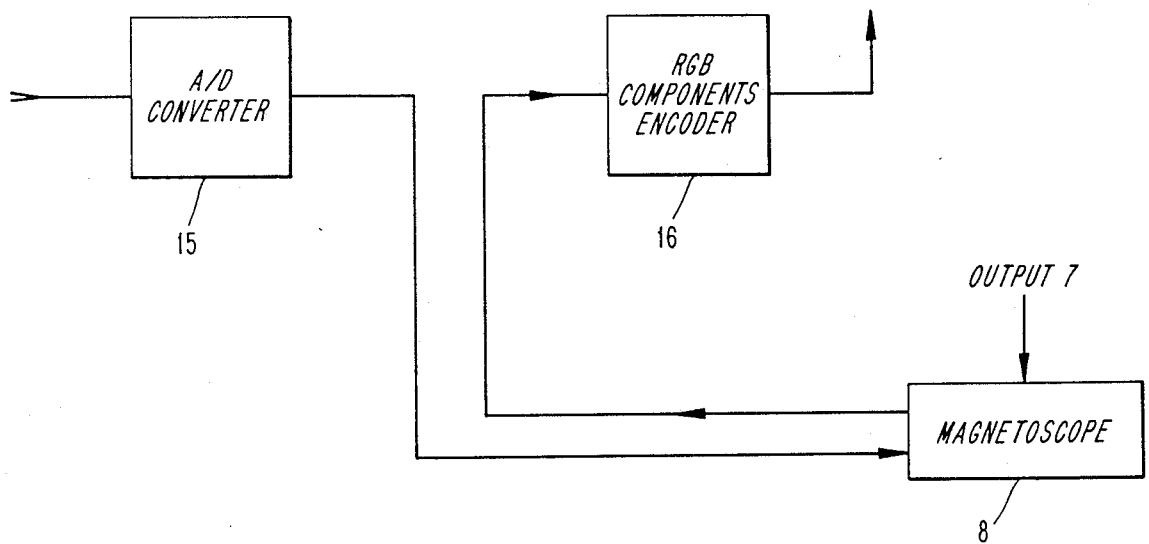
FIG. 3 is a partial diagram showing a modification of the video frequency meter shown in FIG. 2.

According to a modification shown in FIG. 3, the analog-digital converter 15 is connected to the input for recording on an audio track of the magnetoscope 8, the reading output of the audio track of the latter being connected to the input of the video encoding circuit.

In this case, the audio track of the magnetoscope 8 constitutes a memory of the signals relating to the activity of the supervised organ.

The reading of these signals could be effected in deferred time in synchronism with the corresponding images of the patient.

Figure 4:
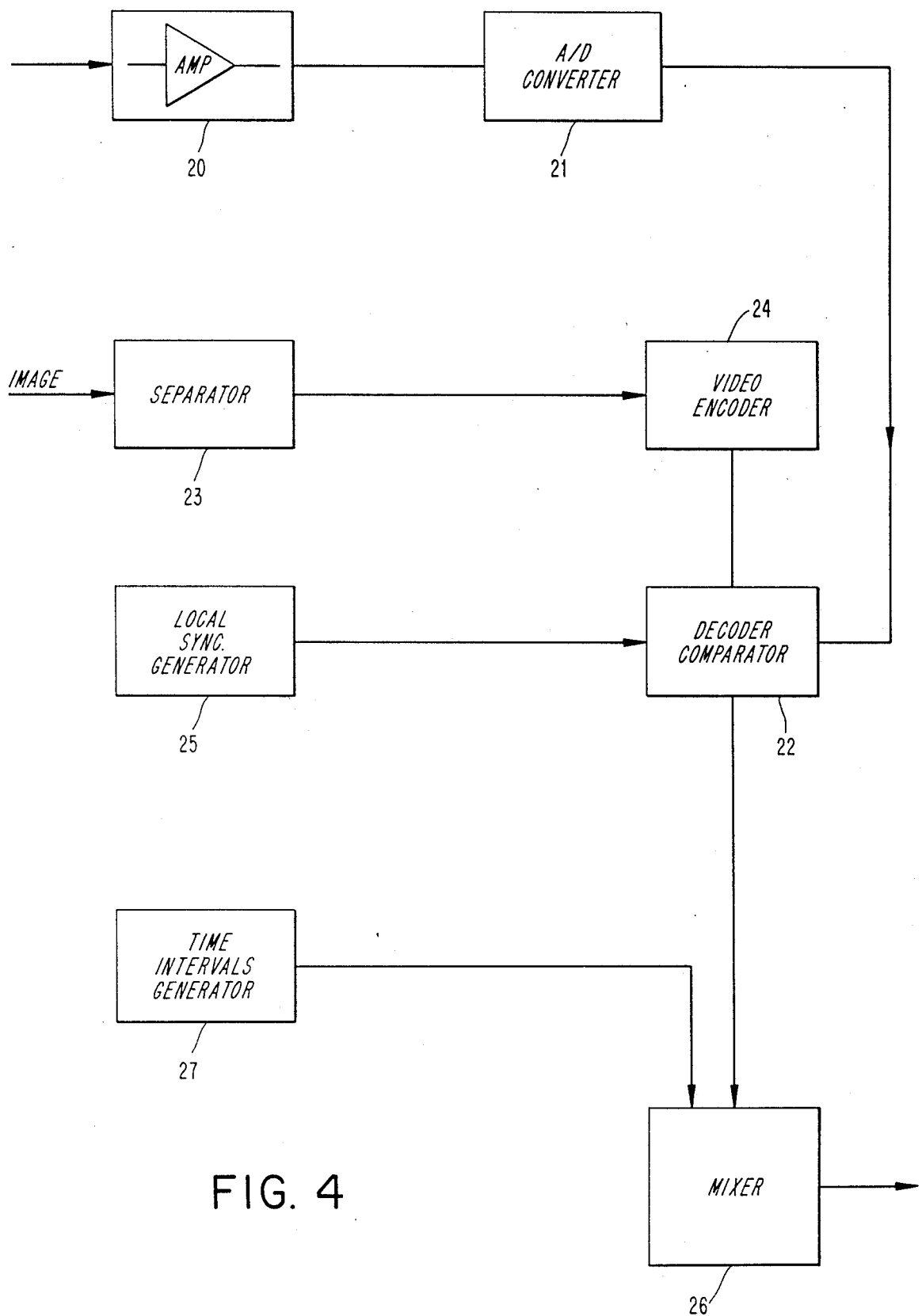
FIG. 4 is a detailed diagram of the video curve converting device which is part of the construction of the device shown in FIG. 1.

The video curve converter shown in FIG. 4 comprises an analog input constituted by the input of an amplifier 20 of the output signals of the receiver 3. The output of the amplifier is connected to the input of an analog-digital converter 21 whose output is connected to the input of a decoder-comparator 22.

The video curve converter further comprises a video input connected to the output of a video frequency meter 6 (FIG. 1).

This video input is the input of a separator 23 whose output is connected to the input of a video encoder 24.

The separator 23 has for function to eliminate the synchronization signal of the input composite signal.

A local synchronization signal generator 25 has its output connected to the synchronization input of the comparator-decoder 22.

The output of the comparator decoder 22 is connected to an input of a signal mixer 26 which is moreover connected, through another of its inputs, to the output of a generator 27 of signals of intervals of time, for example of 1 second.

The output of the mixer 26 is connected to the corresponding input of the magnetoscope 8 and therefore constitutes the output of the video curve converter 7.

As a modification, the output of the amplifier 20 may be directly connected to an input for recording onto an audio track of the magnestocope 8, the corresponding reading output of the latter being then connected to the input of the analog-digital converter 21. Such an arrangement permits a direct recording of the signals representing the activity of the supervised organ and a deferred reading of the signals in synchronism with the corresponding images showing the motions of the patient.

The device just described operates in the following manner:

The patient, who carries on him the sensors 1 suitably disposed with respect to the organ to be supervised, for example the heart, and the transmitter 2, moves in a zone within the field of the video camera 4. This zone may be, for example, a swimming pool in which the patient carries out swimming exercises.

The camera, which is either handled by an operator or associated with a support with means for automatically aiming at the patient, films the motions of the latter.

Simultaneously, the sensors 1 transmit to the transmitter 2, low-frequency signals corresponding to the activity of the supervised organ of said patient.

The transmitter 2 transmits the signals to the receiver 3.

The output signals of the video camera 4 are applied to the input of the video clock 5 which delivers at its output a composite signal. This composite signal includes synchronization and chronometric video data, the latter enabling the practicioner to locate in the carried recording out the interval of time of interest for the purpose of proceeding to detailed analyses of the recorded signals during these intervals. The composite signal is applied to the input of the video frequency meter 6 which also receives the output signals from the receiver 3.

In the video frequency meter 6, the composite signal coming from the video clock 5 is separated into a video signal and a synchronization signal. The video signal, amplified by the amplifier 11, is applied to the mixing circuit 12.

The output signal of the receiver 3 is converted into a digital signal and counted so that the output digital signal of the converter 15 corresponds to the instantaneous value of the number of pulsations of the heart by unit of time.

The output signal of the converter 15 is converted into a video analog signal in the digital-analog converter 16, decoded in the circuit 16a and applied to the mixing circuit 12.

The latter delivers at its output a signal which is the result of the superposition of the video signals coming from the camera and resulting from the conversion of the output signals of the receiver 3 corresponding to the activity of the supervised organ.

This output signal is applied to an input of the circuit 14 for reconstituting a composite signal, which receives at its other input the synchronization signal from the separator 10.

The output signal of the circuit 14 constitutes, after amplification, the signal to be transmitted to the video curve converter 7.

This signal contains the numerical data relating to the patient heart rhythm adapted to be recorded by the magnetoscope 8 and to appear clearly on the display screen 9.

It is applied to the input of the separator circuit 23 whose output signal only comprises the video signal alone.

This signal is in turn applied to the input of the video encoder 24.

The output signal of said encoder is applied to the corresponding input of the comparator-decoder 22.

The output signal of the transmitter 3 (FIG. 1) is applied to the input of the amplifier 20.

After amplification, this signal is converted into a digital TTL signal and applied to the corresponding input of the comparator-decoder 22.

The output signal of the comparator 22 contains all the data in the video form of the image of the patient in the course of his activity, of the numerical value of the heart rhythm, and of the diagram as a function of time operation of the heart.

This signal is rendered composite by means of the synchronization signal coming from the synchronization signal generator 25. It is applied to the signal mixer 26 which receives also a time interval signal generated by the generator 27.

The mixer 26 ensures the distribution of the signals of various types contained in the video signal and its output signal is applied to the magnetoscope 8 so as to be recorded and then to the display device 9. Appearing simultaneously on the screen of the latter are the image of the patient in motion, the instantaneous numerical value of his heart rhythm, the date and the hour at which the recording took place, and the diagram as a function of time of the heart activity of the patient plotted against a time scale of one second appearing as abscissae in this diagram.

Figure 5:
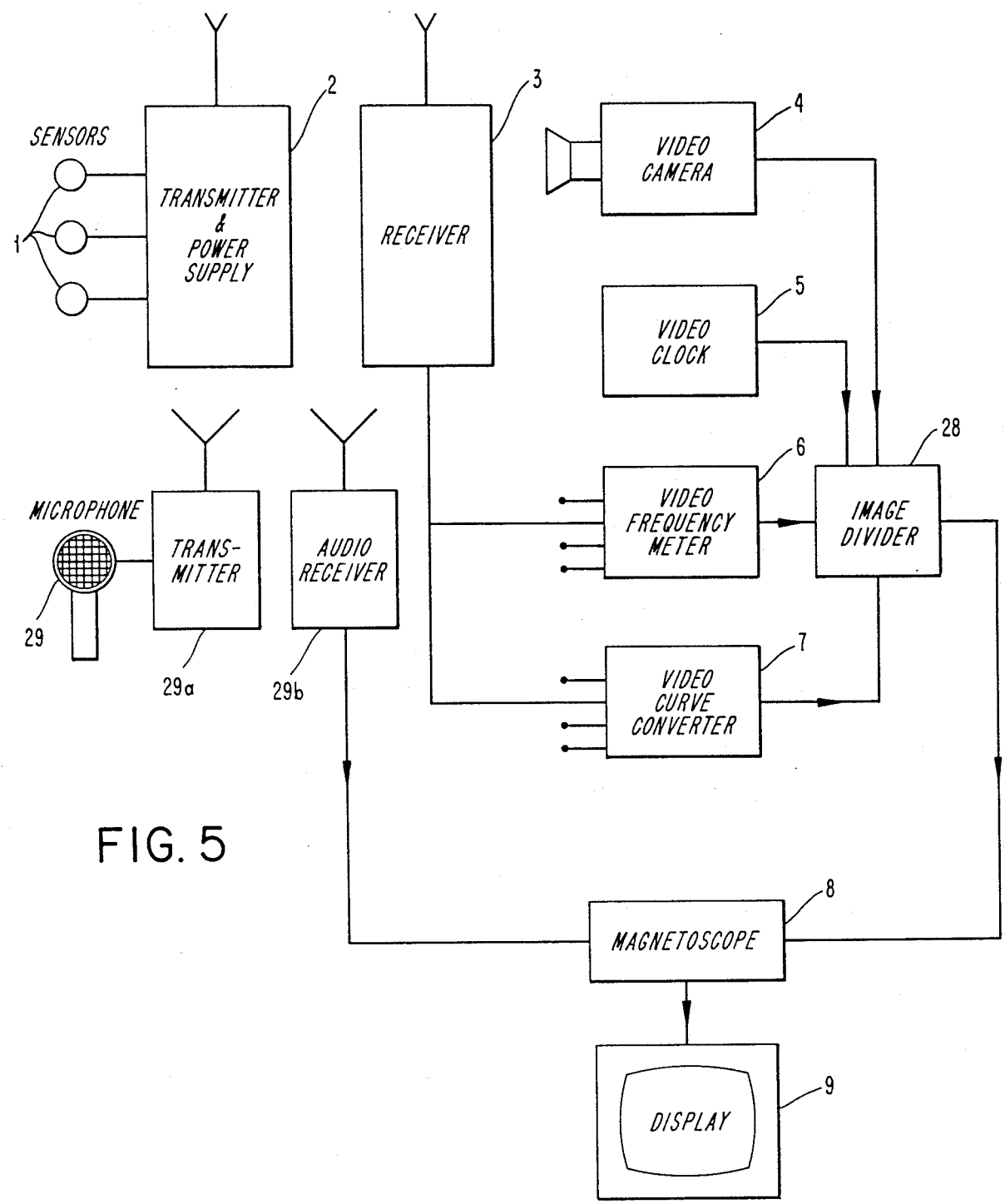
FIG. 5 is a block diagram of another embodiment of the observing and recording device shown in FIG. 1.

FIG. 5 shows another embodiment of the device according to the invention.

In this Figure, the elements of the device identical to those of the device of FIG. 1, are designated by the same reference characters.

This device comprises sensors 1 connected to a transmitter 2 having an autonomous power supply carried by the patient. A receiver 3 of the signals from the transmitter 2 is connected to a video frequency meter 6 and to a video curve converter 7.

The device further comprises a video camera 4 and a video clock 5.

The camera 4, the clock 5, the video frequency meter 6 and the video curve converter 7 are connected to corresponding inputs of a circuit 28 for dividing up the image.

The dividing up circuit 28 ensures the distribution of the various video data contained in the output signals of the circuits 6 and 7 for their display in corresponding zones of the screen of the display 9 connected to the magnetoscope 8 to which the output of the dividing up circuit 28 is connected.

The device shown in FIG. 5 comprises a microphone 29 which may be carried by the patient for making commentaries on his sensations in the course of the examination.

The microphone is connected to a transmitter 29a associated with an audio receiver 29b connected to an audio recording track of the magnetoscope 8 which records the data given by the patient simultaneously with the images of his activity.

During the reading, these data can be of utility for completing the analysis of the practitioner.

It will be understood that such a microphone associated with the corresponding transmission means may also be associated with the device shown in FIG. 1.

Figure 5A:
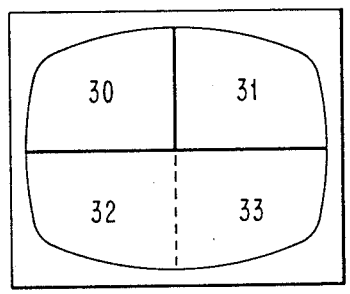
FIG. 5A shows the division of the screen of the display device shown in FIG. 5.

The distribution ensured by the dividing up circuit 28 is shown in FIG. 5A which diagrammatically represents the surface of the screen of the display device 9.

The upper left part 30 of the screen is reserved for the display of the image of the patient, the upper right part 31 is for the display of the numerical values of the heart rhythm, of the hour and other useful data coming possibly from other inputs of the video frequencymeter 6 which are then connected to data-receiving devices relating to these other numerical data.

The lower parts 32, 33 are provided for the display of the diagram as a function of time of the activity of the heart.

In the embodiments just described, the sensors 1 are connected to a common transmitter 2. However, it is possible to envisage associating a transmitter with each sensor, which would permit the avoidance of the carrying of a relatively large transmitter by the patient, provided these circuits are miniaturized.

The embodiments just described are considered to be applicable to the observation and recording of cardiological phenomena for the purpose of the study and the supervision of heart diseases.

However, it will be understood that this device may also be applied to the study of organs other than the heart, provided that the activity of the concerned organ may be converted into electrically recordable signals.

The invention may also be applied to the study of the behaviour of high-level sportsmen while taking into account factors of the environment in which they move.

The device according to the invention is designed for a thorough miniaturization.

It is for example possible to integrate in the camera the receiver 3, the clock 5, the video frequency meter 6 and the video converter 7.

What is claimed is:

1. A device for observing and recording activity of at least an organ of the body of a patient producing electrically recordable manifestations, for the purpose of in particular studying and supervising heart diseases, comprising video means for filming motions of the patient which is free to move within a determined space such as a swimming pool, means for detecting and transmitting electrical signals produced by the activity of said organ, means for combining video signals corresponding to an image of the patient with the electrical signals produced by the activity of said organ, means for recording said combined signals, and means for simultaneously displaying images relating to the motions of the patient within said space and images of the electrical signals produced by the activity of said organ, said means for detecting and transmitting the electrical signals produced by the activity of said organ comprising sensors fastened to the body of the patient so as to receive data relating to the activity of said organ, a transmitter carried by the patient and connected to the sensors, an autonomous electrical power supply connected to the transmitter, a receiver for receiving the signals from the transmitter, a video curve converter, a video frequency meter, said receiver being connected to an input of the video curve converter which has another input connected to an output of the video filming means, the video curve converter being adapted to permit a synchronized recording and/or observation of images relating to the motions of the patient within said space filmed by the video filming means and images of a diagram as a function of time of the operation of said organ, the receiver being furthermore connected to an input of the video frequency meter which has another input connected to an output of the video filming means, the frequency meter being adapted to permit the synchronized recording and/or observation of the images relating to the motions of the patient filmed by the video filming means, and images of numerical data relating to the operation of said organ.

2. A device according to claim 1, wherein the video frequency meter and the video curve converter are connected in series between the filming means and the video recording means.

3. A device according to claim 1, comprising an image dividing up means, outputs of the video frequency meter and the video curve converter being connected to separate inputs of the image dividing up means which has another input connected to an output of the filming means, an output of the image dividing up means being connected to the video recording means.

4. A device according to claim 1, wherein the video curve converter comprises an analog-digital converter of the signals coming from said receiver, a decoder comparator, a video encoder, and a separator circuit for separating signals coming from the video filming means, the analogdigital converter being connected to an input of the decoder-comparator which has another input which is connected to an output of the video encoder which has an input which receives output video signals of the separator circuit.

5. A device according to claim 1, wherein the video frequency meter comprises a mixing circuit, a separator circuit and means converting the output signals of the receiver into video signals, the mixing circuit having an input connected to an output of the separator circuit for separating the signals coming from the filming means, the mixing circuit having another input which is connected to the means for converting the output signals of the receiver into video signals.

6. A device according to claim 5, wherein said means for converting the output signals of the receiver into video signals comprise a video encoding circuit, a decoding circuit and an analog-digital converter which has an input connected to the receiver and an output connected to the video encoding circuit, an output of the video encoding circuit being connected to a corresponding input of the mixing circuit through the decoding circuit.

7. A device according to claim 6, wherein the output of the analog-digital converter is connected to a recording input for recording on an audio track of the video recording means, the corresponding reading output of the video recording means being connected to the input of said video encoding circuit.

8. A device according to claim 4, wherein the input of the video curve converter adapted to receive the signals from the receiver is connected to a recording input for recording on an audio track of the video recording means, the corresponding output of the video recording means being connected to the input of the analog-digital converter.

9. A device according to claim 1, further comprising a transmitter carried by the patient and a microphone connected to a receiver of the signals from said transmitter associated with the microphone, said receiver being connected to a recording input for recording on an audio track of the video recording means.

10. A device according to claim 1, wherein the video frequency meter and/or the video curve converter comprise a plurality of inputs similar to the input connected to the receiver and adapted to receive signals relating to the activity of other organs of the patient.

11. A device according to claim 1, wherein the video frequency meter and/or the video curve converter comprise a plurality of inputs similar to the input connected to the receiver and adapted to receive signals relating to the activity of similar organs of a plurality of patients.

12. A device according to claim 1, wherein the video frequency meter and/or the video curve converter comprise a plurality of inputs similar to the input connected to the receiver and adapted to receive parameters of the environment in which the patient moves.

* * * * *